(12) United States Patent
Norcini et al.

(10) Patent No.: US 7,482,392 B2
(45) Date of Patent: Jan. 27, 2009

(54) WHITE SOLID PHOTOINITIATOR IN THE FORM OF POWDER AND PREPARATION THEREOF

(75) Inventors: Gabriele Norcini, Comabbio (IT); Stefano Romagnano, Gallarate (IT); Marco Visconti, Varese (IT); Gluseppe Li Bassi, Gavirate (IT)

(73) Assignee: Lamberti SpA, Albizzate (IT)

( * ) Notice: Subject to any disclaimer, the term of this patent is extended or adjusted under 35 U.S.C. 154(b) by 463 days.

(21) Appl. No.: 10/577,194

(22) PCT Filed: Oct. 14, 2004

(86) PCT No.: PCT/EP2004/052532

§ 371 (c)(1), (2), (4) Date: Apr. 26, 2006

(87) PCT Pub. No.: WO2005/040083

PCT Pub. Date: May 6, 2005

(65) Prior Publication Data

US 2007/0135531 A1    Jun. 14, 2007

(30) Foreign Application Priority Data

Oct. 27, 2003    (IT) .......................... VA2003A0040

(51) Int. Cl.
*C08F 2/50* (2006.01)
*C07C 49/00* (2006.01)
*C07C 49/17* (2006.01)
*C07C 45/00* (2006.01)
*C07C 45/46* (2006.01)

(52) U.S. Cl. ........................... 522/42; 522/14; 522/103; 522/107; 522/173; 568/337; 568/347

(58) Field of Classification Search ................... 522/14, 522/42, 103, 107, 173; 568/337, 336, 335
See application file for complete search history.

(56) References Cited

U.S. PATENT DOCUMENTS

| 4,308,400 A |  | 12/1981 | Felder et al. |
| 4,315,807 A |  | 2/1982 | Felder et al. |
| 4,318,791 A |  | 3/1982 | Felder et al. |
| 4,321,118 A |  | 3/1982 | Felder et al. |
| 4,474,990 A | * | 10/1984 | Jansons ..................... 568/319 |
| 4,861,916 A | * | 8/1989 | Kohler et al. ............... 568/337 |
| 5,118,860 A | * | 6/1992 | Lindley ..................... 568/323 |

FOREIGN PATENT DOCUMENTS

EP        0 003 002        7/1979

* cited by examiner

*Primary Examiner*—Susan W Berman
(74) *Attorney, Agent, or Firm*—Madan, Mossman & Sriram, P.C.

(57) ABSTRACT

The present invention is refereed to a white solid photoinitiator in the form of powder and consisting of 2-hydroxy-1-{4-[4-(2-hydroxy-2-methyl-propionyl)-phenoxy]-phenyl}-2-methyl-propan-1-one (COMPOUND1), and to the procedure for its preparation.

20 Claims, No Drawings

US 7,482,392 B2

WHITE SOLID PHOTOINITIATOR IN THE FORM OF POWDER AND PREPARATION THEREOF

TECHNICAL FIELD

This invention is related to a white solid photoinitiator in the form of powder consisting of 2-hydroxy-1-{4-[4-(2-hydroxy-2-methyl-propionyl)-phenoxy]-phenyl}-2-methyl-propan-1-one (COMPOUND1) and to the procedure for its preparation.

COMPOUND1 obtained through the procedure of the invention is particularly reactive as photoinitiator in photopolymerizable systems and it is easily and completely soluble in such systems in the quantities useful for the photopolymerization.

BACKGROUND ART

The known photopolymerizable systems contain a photoinitiator possessing in the molecule a functional group that, by electromagnetic excitation, generally UV radiation, produces radicals able to polymerize the system.

In EP 3002 A numerous alpha-hydroxyketons are described together with their uses as photoinitiators; particularly in Example 5 the use as photoinitiator of 2-hydroxy-1-{4-[4-(2-hydroxy-2-methyl-propionyl) phenoxy]-phenyl}-2-methyl-propan-1-one (compound No. 21), obtained in form of wax and with boiling point of 220° C. at 0.05 mmHg, is described.

DISCLOSURE OF INVENTION

We have now found that 2-hydroxy-1-{4-[4-(2-hydroxy-2-methyl-propionyl)-phenoxy]-phenyl}-2-methyl-propan-1-one obtained as a white solid in the form of powder is easy to handle and completely soluble in the quantities useful for the photopolymerization in the photopolymerizable systems that contain it as photoinitiator.

It is therefore a fundamental object of the present invention the white solid photoinitiator, in the form of powder, consisting of 2-hydroxy-1-{4-[4-(2-hydroxy-2-methyl-propionyl)-phenoxy]-phenyl}-2-methyl-propan-1-one (COMPOUND1) and having melting point between 96° and 99° C., product not previously described in the literature.

The product of the invention is particularly interesting when used as photoinitiator in formulations either of the transparent or pigmented kind, since it allows to obtain very good photocrosslinking rates, notably higher than those of analogous products normally used and commercially available; moreover it provides good colour stability to photopolymerized transparent systems.

Such characteristics render the product of the invention particularly innovative and desirable for industrial use because of the high line speed that it allows to practise.

It is a further object of the present invention the procedure for the preparation of 2-hydroxy-1-{4-[4-(2-hydroxy-2-methyl-propionyl)-phenoxy]-phenyl}-2-methyl-propan-1-one as white solid in the form of powder (COMPOUND1) including the following steps:

a) Friedel Crafts reaction of diphenylether with an acylating agent selected between alpha-bromoisobutyril bromide and alpha-chloroisobutyril chloride, catalyzed by Lewis acids;

b) reaction of 2-bromo-1-{4-[4-(2-bromo-2-methyl-propionyl)-phenoxy]-phenyl}-2-methyl-propan-1-one (or of 2-chloro-1-{4-[4-(2-chloro-2-methyl-propionyl)phenoxy]-phenyl}-2-methyl-propan-1-one) obtained in step a) with hydrated bases, at a temperature comprised between 10° C. and 50° C., preferably between 15° C. and 40° C., to give 2-hydroxy-1-{4-[4-(2-hydroxy-2-methyl-propionyl)-phenoxy]-phenyl}-2-methyl-propan-1-one dissolved in solvent;

c) cristallization of the thus obtained product.

The Friedel Crafts reaction of step a) is performed preparing a solution of acylating agent and diphenylether, in a molar ratio comprised between 2.0 and 2.2, in dichloromethane or other solvent, as, by way of example, chlorobenzene, and then adding the Lewis acid, preferably $AlCl_3$, in portions to the solution, maintaining the temperature between −20° C. and 20° C., preferably between −5° C. and 5° C.

The Friedel Crafts reaction of step a) normally includes a final quenching phase, wherein the reaction mixture is poured in diluted acidic water solution, the separation of phases and the washings of the organic phase (where the reaction product is dissolved) with water or brine; such organic phase can be used as such in step b), or after evaporation of the solvent.

The reaction mixture of step b) can be indifferently monophasic or biphasic according to the solvent used; whenever the reaction mixture is biphasic, it is preferable to add a phase transfer catalyst such as benzyltriethylammonium chloride (BTEAC).

In the preferred forms of realization of the invention, the solvent of step a) is evaporated before proceeding with step b) and the product of reaction of step a) is dissolved in an aliphatic alcohol miscible with water, particularly in isopropanol.

The hydrated base commonly used in step b) is selected among NaOH, KOH or $Ba(OH)_2$ in aqueous solution at 20-50% w/w; preferably the hydrated base is NaOH.

According to a fundamental aspect of the procedure according to the invention, COMPOUND1 is directly obtained by crystallization from the reaction mixture.

The crystallization takes place from the solvent in which 2-hydroxy-1-{4-[(2-hydroxy-2-methyl-propionyl)-phenoxy]-phenyl}-2-methyl-propan-1-one is dissolved after step b), through partial distillation of the solvent and cooling or through partial evaporation of the solvent and dilution with lipophilic solvents, such as petroleum ether or hexane.

COMPOUND1 can be also obtained by precipitation, filtration and drying, by adding to the residue obtained after evaporation of the solvent at the end of step b) one or more solvents selected among: ethyl acetate and toluene, both as such or in mixture with petroleum ether; isopropanol, n-propanol, ethyl alcohol or mixtures thereof, optionally in mixture with water; n-butyl alcohol; isobutyl alcohol; t-butyl alcohol.

In the preferred forms of realization of the invention, when the reaction of step b) is performed in an alcohol miscible with water, such as isopropanol, 2-hydroxy-1-{4-[4-(2-hydroxy-2methyl-propionyl)-phenoxy]-phenyl}-2-methyl-propan-1-one is obtained as a white solid in the form of powder with a melting point between 96 and 99° C. (COMPOUND1) by the following phases: addition of from 0.5 to 2.0 parts by weight of water for every part by weight of isopropanol at the end of the reaction of step b) cooling at a temperature between 0° C. and 10° C.; collecting by filtration the thus obtained precipitate; drying at a temperature comprised between 20° C. and 60° C.

COMPOUND1 according to the invention is a white solid photoinitiator in the form of powder having a melting point between 96° and 99° C., it is easily soluble in the photopolymerizable systems in the quantities normally used for photopolymerization, and it mainly consists of the para-para isomer, 2-hydroxy-1-{4-[4-(2-hydroxy-2-methyl-propionyl)- phenoxy]-phenyl}-2-methyl-propan-1-one; 300 MHz $^1$H-NMR do not indicate the presence of the other isomers.

In the present text, with the expression "photopolymerizable system" or "photopolymerizable formulation", we mean a mixture of reactive monomers and/or oligomers, at least a photoinitiator, fillers, dispersants and other additives of general use.

The term "photopolymerization" has a broad meaning and comprises, for example, the further polymerization or crosslinking of polymeric material, for example pre-polymers, the homo-polymerization and the copolymerization of simple monomers and the combination of these types of reactions.

Useful monomers for photopolymerizable systems include, for example: acrylonitrile, acrylamide and derivatives thereof, vinyl ethers, N-vinylpirrolidone, mono and polyfunctional allyl ethers such as trimethylolpropanediallyl ether, styrene and alpha-methylstyrene, esters of acrylic and methacrylic acid with aliphatic alcohols, with glycols, with polyhydroxylates compounds such as pentaerythritol and trimethylolpropane or with aminoalcohols, esters of vinyl alcohol with aliphatic or acrylic acids, derivatives of fumaric and maleic acid.

Useful oligomers for photopolymerizable systems are for example: polyesters, polyacrylates, polyurethanes, epoxidic resins, polyethers with acrylic, maleic or fumaric functionality.

COMPOUND1 of the invention acts as photoinitiator and can be used alone or in combination with other photoinitiators such as for example benzophenone and its derivatives (such as methylbenzophenone, trimethylbenzophenone), acetophenone and its derivatives, for example alpha-hydroxyacetophenones, alpha-aminoacetophenones, di-alkoxyacetophenones, (such as oligo-[2-hydroxy-2-methyl-[4-(1-methylvinyl)phenyl]-propanone], 2-hydroxy-2-methyl-1-phenyl-propanone, alpha-hydroxycyclohexyl phenyl ketone, 2-hydroxy-1-[4-(2-hydroxy-ethoxy)-phenyl]-2-methyl-propan-1-one, 2-dimethylamino-2-(4-methylbenzyl)-1-(4-morfolin-4-yl-phenylybutan-1-one, 2-benzyl-2-dimetilamino-1-(3,4-dimetossi-phenyl)butan-1-one, 2-benzyl-2-dimethylamino-1-(4-morfolin-4-yl-phenyl)-butan-1-one, 2-methyl-1-(4-methylsulfanyl-phenyl)-2-morfolin-4yl-propan-1-one, 1-[2,3-dihydro-1-[4-(2-hydroxy-2-methyl-1-oxopropyl)phenyl]-1,3,3-trimethyl-1H-inden-5-yl]-2-hydroxy -2-methyl-1-propanone, 1-[2,3-dihydro-3-[4(2-hydroxy-2-methyl-1-oxopropyl)phenyl]-1,1,3-trimethyl-1H-inden-5yl]-2-hydroxy-2-ethyl-1-propanone, 4,3'-bis(alpha,alpha-hydroxy-isobutyryl)-diphenylmethane, 4,4'-bis(alpha,alpha-hydroxy-isobutyryl)-diphenylmethane, ketosulphones (such as 1-[4-(4-benzoyl-phenylsulfanyl)-phenyl]-2-methyl-2-(toluene-4-sulfonyl)-propan-1-one), benzoin ethers, benzyl ketals (such as benzyl dimethyl ketal), phenylglyoxylate and its derivatives (such as phenylglyoxylic acid methylester, ethyl ester of 2-(2-oxo-2-phenylacetoxy-ethoxyethyl) oxyphenylacetic acid), monoacylphosphine oxides, such as (2,4,6-trimethylbenzoyl)-diphenyl-phosphine oxide or the ethyl ester of phenyl-(2,4,6-trimethylbenzoyl)-phosphinic acid, bisacylphosphine oxides, (such as bis-(2,6dimethoxybenzoyl)-(2,4,4-trimethyl-pent-1-yl) phosphine oxide, bis(2,4,6-trimethylbenzoyl)-phenyl-phosphine oxide, bis(2,4,6-trimethylbenzoyl)-(2,4-dipentoxyphenyl)phosphine oxide), trisacylphosphine oxides, halogenomethyltriazine, ferrocene derivatives or titanocenes, photoinitiators containing the borate or O-acyloxymic group, sulphonium, phosphonium or aromatic iodonium salts.

The utilisation of COMPOUND1 of the invention with tertiary amines (such as the triethylamine, N-methyldiethanolamine, esters of p-dimethylamino benzoic acid), that increase the speed of crosslinking by reducing the inhibitory effect of oxygen, is particularly advantageous.

Besides COMPOUND1 of the invention, many components can be included in the photopolymerizable systems, for example thermal stabilizers, dyes or pigments, sensitisers, photooxydation stabilizers as sterically hindered amines, antioxidants, oxygen inhibitors, thermal radicals generators such as organic and inorganic peroxides, peresters, hydmperoxides, benzopinacols, azoderivatives such as azaisobutyronitrile, metallic compounds such as cobalt(II) salts, manganese, antifoam, fillers, glass and carbon fibres, Uxotropic agents.

Other components that can be included are non-photopolymerizable polymers present as inactive substances, as for example nitrocellulose, polyacrylic esters, polyolefines etc., or polymers that are crosslinkable with other systems (for example with peroxides, atmospheric oxygen, acid catalysts or thermal activation) such as polyisocyanates, urea, melamine or epoxidic resins.

COMPOUND1 of the invention is generally used in the photopolymerizable system in a quantity of 0.01 to 20% by weight, preferably of 0.5 to 5% by weight, on the total weight of the photopolymerizable system, and it is highly compatible with the system, while imparting to it an increased photochemical reactivity.

It is a further object of the present invention a method for the preparation of a photopolymerizable system through solubilization of the white solid photoinitiator in the form of powder, with a melting point between 96° and 99° C., consisting of 2-hydroxy-1-{4-[4-(2-hydroxy-2-methyl-propionyl)-phenoxy]-phenyl}-2-methyl-propan-1-one, (COMPOUND1), in a quantity of 0.01 to 20% by weight, preferably of 0.5 to 5% by weight, in one or more reactive ethylenically unsaturated monomer and/or oligomer at a temperature between 20 and 60° C.

Examples of sources of light useful for the photopolymerization of the photopolymerizable systems prepared according to the invention are mercury vapour or superactinic or excimers lamps, with emission bands in the UV-visible region.

Among the possible useful sources of light, sunlight and other artificial sources emitting electromagnetic radiation with a wavelenght from 180 nm up to the IR region are also included.

COMPOUND1 according to the invention acts as an efficient photoinitiator both in transparent systems and, surprisingly, in pigmented systems, and it is for instance useful for the preparation of photocrosslinkable inks, in photopolymerizable formulations for wood coating, paper, plastics, metals, in overprint coating systems, in printing inks, in varnishes, in powder coating, in the electronics, for instance for the production of printed circuits, in microelectronic and in general in all those applications in which it is useful the formation of radicals through electromagnetic radiation.

It is therefore a further object of the invention a method for the coating of wooden surfaces, of paper, cardboard, plastics or metal through the application of a photo-crosslinkable system prepared by dissolution of the white solid photoinitiator in the form of powder having a melting point between 96° and 99° C. and consisting of 2-hydroxy-1-{4-[4-(2-hydroxy-2-methyl-propionyl)-phenoxy]-phenyl}-2-methyl-propan-1-one, (COMPOUND1), in one or more reactive ethylenically unsaturated monomers and/or oligomers and the subsequent photopolymerization with a source of light with emission bands in the UV-visible range.

EXAMPLE 1

Preparation of COMPOUND1

I. Synthesis of 2-bromo-1-{4-[4-(2-bromo-2-methyl-propionyl)-phenoxy]-phenyl}-2-methyl-propan-1-one.

To a solution of 5 g (29.37 mmols) of diphenylether and 15.23 g (64.61 mmols) of alpha-bromoisobutrylbromide (purity 97.5% by weight) in 50 ml of dichloromethane in about 30' 8.61 g (64.61 mmols) of aluminum trichloride were added, maintaining the temperature between 0° and 5° C. After 1.5 h the reaction mixture was poured in a mixture of 200 ml of water and ice and 4 ml of 37% HCl. The organic phase was separated and washed with brine, dried on sodium sulphate, and filtered, A sample obtained after evaporation of the solvent was analysed.

NMR (300 MHz, $CDCl_3$, δ ppm): 8.25 (d, 4H); 7.1 (d, 4H); 2.07 (s, 12H).

II. Synthesis of 2-hydroxy-1-{4-[4-(2-hydroxy-2-methyl-propionyl)-phenoxy]-phenyl}-2-methyl-propan-1-one.

To the solution of 2-Bromo-1-[4-4(2-bromo-2-methyl-propionyl)-phenoxy]-phenyl-2-methyl-propan-1-one 13.75 g (29.37 mmol) 8.46 g (105.73 mmol) of NaOH at 50%, 137 mg of BTEAC at 50% and 50 ml of dichloromethane were added, and the solution refluxed for 2 h. After dilution with 50 ml of water and 50 ml of dichloromethane, the phases were separated. The organic phase was washed with water and with a solution of NaCl, dried on sodium sulphate and filtered off.

Crystallization of COMPOUND1.

The solvent was partially evaporated from the solution obtained in II to a residual volume of 25-30 ml. By cooling, 2-hydroxy-1-{4-[4-(2-hydroxy-2-methyl-propionyl)phenoxy]-phenyl}-2-methyl-propan-1-one was separated as a white solid, filtered and vacuum dried at 50° C.; 4.9 g of powder having m.p. 96°-98 ° C. are obtained (COMPOUND1).

$^1$H-NMR analysis at 300 MHz does not show the presence of other isomers.

Part of the product was crystallized from toluene, obtaining a product with a melting point of 97°-99 ° C.

NMR (300 MHz, $CDCl_3$, δ ppm): 8.10 (d, 4H); 7.07 (d, 4H); 3.9, (s, 2H); 1.63 (s, 12H).

EXAMPLE 2

Preparation of COMPOUND1

I. Synthesis of 2-bromo-1-{4-[4-(2-bromo-2-methyl-propionyl)-phenoxy]-phenyl}-2-methyl-propan-1-one The reaction was performed as described as in Example 1 (I.), starting from 45.26 g of diphenylether.

II. Synthesis of 2-hydroxy-1-{4-[4-(2-hydroxy-2-methyl-propionyl)-phenoxy]-phenyl}-2-methyl-propan-1-one.

From the solution obtained in I the solvent was evaporated under vacuum thus obtaining 131.25 g of an oil that spontaneously solidifies. The crude material so obtained is mixed under stirring with 250 ml of isopropyl alcohol then at room temperature 44.8 g of 50% NaOH (0.56 mol) were added. After 1 h at room temperature under stirring the precipitate was filtered off and the solution acidified to pH 2-3 with 1M HCl.

III. Cristallization of COMPOUND1.

350 ml of water were added to the thus obtained solution and the mixture was cooled to 0-10° C., obtaining a white precipitate that was easily filtered and dried in oven at 50° C.; 82.17 g of product were obtained (COMPOUND1).

m.p.=97-98° C.

$^1$H-NMR analysis at 300 MHz does not show the presence of other isomers.

NMR (300 MHz, $CDCl_3$, δ ppm): 8.10 (d, 4H); 7.07 (d, 4H); 3.9 (s, 2H); 1.63 (s, 12H).

EXAMPLE 3

Application Tests

The substances used for the preparation of the photopolymerizable systems evaluated in the following application tests are:

Ebecryl® 220 (hexafunctional aromatic urethane acrylate from UCB (Belgium);

OTA 480® (trifunctional oligomer acrylate derived from glycerol, from UCB, Belgium);

HDDA, (1,6-hexanedioldiacrylate from UCB, Belgium);

TMPTA (trimethylolpropanetriacrylate);

Ebecryl® 600 (epoxyacrylate from UCB, Belgium);

Ebecryl® 810 (polyester acrylate from UCB, Belgium);

TPGDA (tripropyleneglycoldiacrylate);

Ebecryl® 350 (additive from UCB, Belgium);

Irgalite® Blue BSNF from CIBA Specialty Chemicals;

Verol 368 (dispersant from Lamberti SpA, Italy)

As photoinitiator, the following compounds have been used:

COMPOUND1 obtained as described in Example 1.

Irgacure® 184, alpha-hydroxyketone commercialised by Ciba Specialty Chemicals.

Irgacure® 907, aromatic aminoketone commercialised by CIBA Specialty Chemicals.

Four formulations (I, II, III and IV) were prepared mixing respectively (% by weight):

| | | |
|---|---|---|
| I. | Ebecryl ® 600 | 40% |
| | TMPTA | 30% |
| | OTA 480 | 30% |
| II. | Ebecryl 220 ® | 75% |
| | OTA 480 ® | 12.5% |
| | HDDA | 12.5% |
| III. | Ebecryl ® 810 | 80.0% |
| | TPGDA | 20.0% |
| IV. | Irgalite ® Blue BSNF | 18.0% |
| | Ebecryl ® 600 | 37.3% |
| | Ebecryl ® 350 | 0.9% |
| | Ebecryl ® 220 | 10.4% |
| | TMPTA | 31.9% |
| | Verol 368 | 1.5% |

The photopolymerizable systems (Ia, Ib, IIa, IIb, IIIa, IIIb, IVa, IVb) were prepared dissolving the photoinitiators in the corresponding formulations (I, II, III and IV) at room temperature; the compositions of such systems (% w/w) are reported in Table 1.

TABLE 1

| | Photopolymerizable systems | | | | | | | |
|---|---|---|---|---|---|---|---|---|
| | Ia | Ib | IIa | IIb | IIIa | IIIb | IVa | IVb |
| Formulation | 96 | 96 | 96 | 96 | 96 | 96 | 97 | 97 |
| COMPOUND1 | 4 | — | 4 | — | 4 | — | 3 | — |
| Irgacure ® 184 | — | 4 | — | 4 | — | 4 | — | — |
| Irgacure ® 907 | — | — | — | — | — | — | — | 3 |

The evaluation of the photopolymerizable systems was made by determining the reactivity parameters and the yellow and white indexes.

Reactivity

The photopolymerizable system is spread with a thickness of 50 microns on a varnished cardboard (3 microns only for the evaluation of the systems IVa and IVb) using a bar-coater and irradiated at a distance of 12 cm from the light source. A Fusion® photopolymerizator was used, equipped with a medium pressure mercury lamp with a power of 120 W/cm.

The photopolymerization rate, measured in m/min, is the maximum possible speed at which a perfect superficial cure of the system is obtained (Tack Free). The perfect superficial cure is intended when the cured layer doesn't show to suffer damages from the "thumb twist test."

The maximum speed (in m/min) at which a damage of the photopolymerized system can't be seen after rubbing with abrasive paper was also measured (Superficial Abrasion); greater is the speed line, greater it is the efficiency of the system.

White and Yellow Index

The photopolymerizable system is spread with a thickness of 50 microns on a varnished cardboard using a bar-coater mounted on an electric stretch-film and therefore is passed at a distance of 12 cm from the light source at a speed of 10 m/mins. A Fusion® photopolymerizator was used, equipped with a medium pressure mercury lamp with a power of 120 W/cm.

White and yellow indexes were measured according to the ASTM standard D 1925-70. A low value of yellow and a high value of white, are index of a good stability of the colour of the formulation.

The results are reported in Table 2.

TABLE 2

| | Tack Free | Superficial Abrasion | Yellow Index | White Index |
|---|---|---|---|---|
| Ia | 48.5 | 35.0 | 10.1 | 56.2 |
| Ib | 22.0 | 15.0 | 10.0 | 56.3 |
| IIa | 58.0 | 45.0 | 10.4 | 55.7 |
| IIb | 28.5 | 18 | 12.8 | 50.8 |
| IIIa | 25.5 | 1.5* | 10.9 | 53.3 |
| IIIb | 9.4 | 4* | 10.6 | 55.1 |
| IVa | 21.0 | — | — | — |
| IVb | 22.0 | — | — | — |

*number of passages (at 10 m/min) necessary not to have a visible damage of the photopolymerized system after rubbing with abrasive paper As shown from the reported data the presence of COMPOUND1 of the invention in the photopolymerizable systems results in a very good curing speed and in a good colour stability (index of yellow and white) of the obtained products.

The invention claimed is:

1. A method for preparing 2-hydroxy-1-{4-[4-(2-hydroxy-2-methyl-propionyl)-phenoxy]-phenyl}-2-methyl-propan-1-one comprising the steps of:
    a) reacting diphenylether with an acylating agent by means of a Friedel-Crafts reaction catalyzed by a Lewis acid to produce a reaction product; and
    b) reacting the reaction product with a hydrated base, at a temperature of from about 10° C. to about 50° C. to produce 2-hydroxy-1-{4-[4-(2-hydroxy-2-methyl-propionyl)-phenoxy]-phenyl}-2-methyl-propan-1-one;
    wherein the acylating agent is selected from the group consisting of alpha-bromoisobutyryl bromide, alpha-chloroisobutyryl chloride, and mixtures thereof.

2. The method of claim 1 wherein the reaction of steps a) or b) takes place in a solvent.

3. The method of claim 2 further comprising recovering the 2-hydroxy-1-{4-[4-(2-hydroxy-2-methyl-propionyl)-phenoxy]-phenyl}-2-methyl-propan-1-one as a white powder.

4. The method of claim 3 wherein the 2-hydroxy-1-{4-[4-(2-hydroxy-2-methyl-propionyl)-phenoxy]-phenyl}-2-methyl-propan-1-one is recovered by a method comprising crystallization.

5. The method of claim 4 wherein the Friedel-Crafts reaction of step a) is performed by:
    i) preparing a solution of the acylating agent and the diphenylether in dichloromethane, at a molar ratio of acylating agent to diphenylether of from 2.0 to 2.2, and then adding the Lewis acid in increments to the solution to form a reaction mixture and maintaining the temperature of the reaction mixture at from about −20° C. to about 20° C.;
    ii) quenching the Friedel-Crafts reaction by pouring the reaction mixture into a dilute acidic water solution, separating the resultant phases into an aqueous phase and an organic phase and washing the organic phase with water or brine; and
    iii) evaporating the dichloromethane in the organic phase to form an intermediate product and then dissolving the intermediate product in a water soluble aliphatic alcohol to form the reaction product.

6. The method of claim 5 wherein the aliphatic alcohol is isopropanol.

7. The method of claim 5 wherein the Lewis acid is $AlCl_3$.

8. The method of claim 6 wherein step b) is performed at a temperature of from about 15° C. to about 40° C.

9. The method of claim 8 wherein the hydrated base is an aqueous NaOH solution and the admixture of the hydrated base and the reaction product forms a product liquor.

10. The method of claim 9 wherein the concentration of NaOH in the aqueous NaOH solution is from about 20 to about 50 percent.

11. The method of claim 9 wherein the crystallization is performed by adding water to the product liquor at a ratio of from about 0.5 to about 2.0 parts by weight of water for every weight part of isopropanol, to form an isopropanol, final product, and water solution.

12. The method of claim 11 further comprising cooling the isopropanol, final product, and water solution to from about 0° to about 10° C.; and collecting 2-hydroxy-1-{4-[4-(2-hydroxy-2-methyl-propionyl)-phenoxy]-phenyl}-2-methyl-propan-1-one by filtration in the form of a filtrate and drying the filtrate at from about 20° to about 60° C.

13. The method of claim 1 wherein the Friedel-Crafts reaction of step a) is performed by:
    i) preparing a solution of the acylating agent and the diphenylether in dichloromethane, at a molar ratio of acylating agent to diphenylether of from 2.0 to 2.2, and then adding the Lewis acid in increments to the solution to form a reaction mixture and maintaining the temperature of the reaction mixture at from about −20° C. to about 20° C.;

ii) quenching the Friedel-Crafts reaction by pouring the reaction mixture into a dilute acidic water solution, separating the resultant phases into an aqueous phase and an organic phase, and then washing the organic phase with water or brine to form a biphasic admixture; and iii. adding a phase transfer catalyst to the biphasic admixture.

14. The method of claim 13 further comprising using the biphasic admixture as the reaction product in step b) and then recovering the 2-hydroxy-1-{4-[4-(2-hydroxy-2-methyl-propionyl)-phenoxy]-phenyl}-2-methyl-propan-1-one by a method comprising crystallization wherein the crystallization is performed by partial distillation of the dichloromethane from the biphasic mixture and then cooling the biphasic mixture; or through partial evaporation of the dichloromethane from the biphasic admixture and then dilution of the biphasic admixture with lipophilic solvents.

15. A white solid photoinitiator composition comprising 2-hydroxy-1-{4-[4-(2-hydroxy-2-methyl-propionyl)-phenoxy]-phenyl}-2-methyl-propan-1-one wherein the 2-hydroxy-1-{4-[4-(2-hydroxy-2-methyl-propionyl)-phenoxy]-phenyl}-2-methyl-propan-1-one is a powder having a melting point of from 96° to 99° C.

16. A photo-crosslinkable system comprising the product of dissolving the white solid photoinitiator composition of claim 15 in at least one ethylenically unsaturated monomer and/or ethylenically unsaturated oligomer at a temperature of from about 20° to about 60° C.

17. The photo-crosslinkable system of claim 16 wherein the white solid photoinitiator is 2-hydroxy-1-{4-[4-(2-hydroxy-2-methyl-propionyl)-phenoxy]-phenyl}-2-methyl-propan-1-one obtained by the method according to claim 15 and is present at a concentration of from about 0.01 to about 20 percent by weight.

18. The photo-crosslinkable system of claim 17 wherein the white solid photoinitiator is present at a concentration of from about 0.5 to about 5 percent by weight.

19. A method for coating a substrate comprising applying the photo-crosslinkable system of claim 16 to a substrate and photo-polymerizing the photo-crosslinkable system with a light source, the light source having emission bands in the UV-visible region.

20. The method of claim 19 wherein the substrate is selected from the group consisting of wood, paper, cardboard, plastic, metal and mixtures thereof.

* * * * *